United States Patent [19]

Krackov

[11] Patent Number: 5,728,898
[45] Date of Patent: Mar. 17, 1998

[54] PROCESS FOR MAKING WATER-SOLUBLE DERIVATIVES OF QUINONES

[75] Inventor: Mark Harry Krackov, West Chester, Pa.

[73] Assignee: Bio-Technical Resources, L.P., Manitowoc, Wis.

[21] Appl. No.: 690,371

[22] Filed: Jun. 27, 1996

[51] Int. Cl.$^6$ .................................................. C07C 39/10
[52] U.S. Cl. ................................. 568/763; 552/208
[58] Field of Search .......................... 568/763; 552/208

[56] References Cited

FOREIGN PATENT DOCUMENTS 08269879  3/1995  Japan .

OTHER PUBLICATIONS

Obtemperanskaya et al; Zh.Anal.Chim. 31(6), 1217–19, 1976.

*Primary Examiner*—Gary Geist
*Assistant Examiner*—Sreeni Padmanabhan

[57] ABSTRACT

Process for making water-soluble hydroquinone salts by reacting an aqueous liquid solution of (a) a formamidine-sulfinic acid and (b) an alkali metal or quaternary ammonium hydroxide in which is dispersed a (c) quinone and water-soluble hydroquinone salts made thereby.

7 Claims, No Drawings

5,728,898

1

PROCESS FOR MAKING WATER-SOLUBLE DERIVATIVES OF QUINONES

FIELD OF INVENTION

The invention is directed to a novel process for making water-soluble derivatives of quinones. In particular, the invention is useful for preparing water-soluble derivatives of 9,10-anthraquinone such as the disodium salt of 9,10-dihydroxyanthracene.

BACKGROUND OF THE INVENTION

Various quinones, which have redox capability, are widely used in many applications in which redox properties and ecological and toxicological safety of the reagent are important. For example, 9,10-anthraquinone is widely used in applications such as reducing microbially induced corrosion in oil pipelines and equipment, reducing $H_2S$ formation in wastewater systems and increasing the yield of fiber when delignifying cellulosic materials.

Because of the effectiveness of such quinones in these and other applications and further in view of the non-toxic nature of such materials, they are becoming more and more in demand. In many of these applications the quinones are used in aqueous systems. Therefore, it is frequently important to use such materials which are substantially soluble in water. Therefore, there has arisen a substantial need for a process by which normally water-insoluble quinones can be converted to substantially water-soluble forms.

SUMMARY OF THE INVENTION

The invention is directed to a process for the preparation of water-soluble salts of hydroquinones comprising reacting an aqueous liquid solution of (a) a formamidinesulfinic acid corresponding to the formula $R_2$ N—C(=NH)—$SO_2H$ in which the R groups are independently selected from the group consisting of H and $C_{1-4}$ alkyl and (b) alkali metal or quaternary ammonium hydroxide having dispersed therein (c) a quinone at a temperature of 10–75 C. under an inert gaseous atmosphere.

DETAILED DESCRIPTION OF THE INVENTION:

In the following discussion, the variables of the reaction system are, for purposes of convenience, discussed in terms of the reactants of primary interest, i.e. 9,10-anthraquinone (AQ), formamidinesulfinic acid (FAS) and sodium hydroxide (base). To the best of applicant's belief, the limits of these variables are also valid with respect to the equivalent compounds discussed herein below.

Formamidinesulfinic acid: Formamidinesulfinic acids which can be used in the process of the invention are those corresponding to the structural formula $R_2N$—C(=NH)—$SO_2H$ in which the R groups are independently selected from hydrogen (H) and $C_{1-4}$ alkyl groups. It is preferred that at least one of the R groups be hydrogen and still further preferred that both R groups be hydrogen. Such formamidinesulfinic acids are solid at room temperature, but quickly dissolve when they are added to an aqueous reaction solution containing alkali metal hydroxide.

Hydroxide Base: Hydroxides of each of the alkali metals can be used in the process of the invention, of which NaOH is preferred because of its better cost effectiveness in this application. It is contemplated that hydroxides of alkaline earth metals might also be used in the invention. However, they are believed to present problems with respect to solubility and therefore are not preferred for use in the invention. Quaternary ammonium hydroxides are also effective in the invention process. Quaternary ammonium compounds, such as $C_{1-4}$ tetraalkylammonium hydroxides are preferred. Mixtures of such hydroxides with metal hydroxides can also be utilized.

Quinones: A wide variety of quinones can be used in the invention. These materials are of major commercial importance because they are redox reagents. Though the process of the invention is applicable to all these materials, it will find major application in making water-soluble derivatives of various anthraquinones, of which 9,10-anthraquinone is most preferred.

Other compounds which can be used include, for example, alkylated quinones such as 2-methylquinone; 2-ethylquinone; 2,3,5-trimethylquinone; 2-methylnaphthoquinone; 2-ethylnaphthoquinone; 2-propylnaphthoquinone; 2-methylanthraquinone; 2-ethylanthraquinone; 2-amylanthraquinone; 2-t-butylanthraquinone; or 2-(4-methyl-pentyl) anthraquinone; an alkenylated quinone compound such as 2-(4-methylpentenyl)anthraquinone; an alkoxylated quinone compound such as 1-methoxyanthraquinone or 1,5-dimethoxyanthraquinone; a phenyl-substituted quinone compound such as 2-phenylquinone; an alkylamino-modified quinone compound such as 2-(N,N-dimethylamino)anthraquinone; or a halogenated quinone compound such as 2-chloroquinone; 2,3-dichloronaphthoquinone; 1-chloroanthraquinone or 2-chloroanthraquinone may, for example, be mentioned.

Reaction Conditions: The reaction of quinones with formamidinesulfinic acids is carried out in the liquid phase even though either or both the quinone and the formamidinesulfinic acid may initially be solid. The acid dissolves quite rapidly in the basic reaction solution while the polycyclic quinones dissolve more slowly and may not take part in the reaction until they are dissolved. The following reaction illustrates the use of 9,10-anthraquinone (AQ) and sodium hydroxide in the invention:

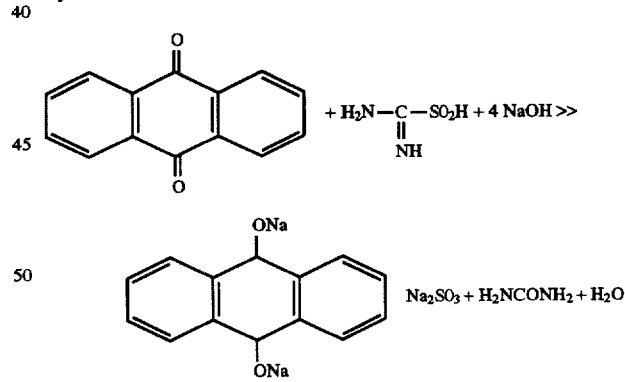

It is preferred that the alkali metal hydroxide be present in the reaction system in at least a stoichiometric amount. That is, it is preferred that the molar ratio of alkali metal hydroxide to AQ be at least 4. Below that ratio, the reaction will be incomplete and therefore less economic. However, molar ratios higher than 4 are quite satisfactory and, in fact, may be preferred in certain instances. Base to AQ ratios up to 8 have been tested and found to give good results. However, no apparent advantage is observed at base/AQ ratios higher than 20.

The molar ratio of FAS to AQ in the reaction system should be at least 1, but to avoid overreduction of the AQ, a large excess should be avoided. A molar excess of 3.5% has been found to be adequate for this purpose. Molar excesses up to at least 20% result in good yields of product.

The temperature at which the invention process is carried out is not particularly critical. In general, it is preferred to run the process at 10–70 C. Within these limits, the reaction rate is quite satisfactory and there is little if any evaporation or thermal degradation of any of the reactants and premature decomposition of FAS in the base is minimized. It is especially preferred to run the process at 20–50 C.

Because the process of the invention is carried out entirely in the liquid phase and no gas is evolved, pressure is not a significant operating variable.

It is, however, preferred also to carry out the process under an inert gas blanket to minimize extraneous oxidation reactions. Nitrogen and argon gases are both suitable for this purpose. Carbon dioxide is not suitable because it is not inert with respect to the base. It is noted that nitrogen gas normally contains small amounts of oxygen, but they do not interfere substantially with the reactions.

EXAMPLES

Example 1

Anthraquinone (104 g, 0.500 mol), 56.8 g (0.525 mol) of formamidinesulfinic acid (FAS), and 364 g of water were charged to a 1 L jacketed, baffled resin flask equipped with a blade stirrer, thermometer, septum-capped sampling port, nitrogen inlet and outlet, and a 250 mL addition funnel. The flask was thoroughly swept with nitrogen gas and maintained under a positive pressure of nitrogen throughout the run. To the vigorously stirred mixture at ambient temperature (23 C) was now added 333 g (~250 mL) of 30% aq sodium hydroxide, at a fast drip over a period of 40 minutes. A moderate exotherm (~10° C.) was experienced during the initial 50–60 mL of caustic addition, due largely to the heat of neutralization of the FAS. After the neutralization was complete (as signaled by the reaction mass rapidly turning dark red), the exotherm moderated significantly, and tempered water was pumped through the jacket to bring the reaction mass to 45 C. The vigorously-stirred reaction mass was held at this temperature for an additional 80 minutes; the course of the reaction was followed by HPLC analysis of mid-run samples taken every twenty minutes.

At the end of the reaction, the dark red reaction mass was transferred, under nitrogen, to a glove bag, where it was filtered and sampled for analysis. HPLC analysis of the filtrate, weighing 833 g, showed it to contain anthrahydroquinone, disodium salt 11.8% (measured as AQ); This constitutes a yield of ~97.3% of theory. The solution also contained 0.08% sodium anthranolate (measured as anthrone). The caustic-insoluble solids filtered out of the reaction mass weighed 0.82 g and contained 14.67% AQ and 0.65% anthrone. No attempt was made to identify the remainder of the solids, which appeared to be impurities in the starting material.

A slow build-up with time of sodium anthranolate, the over-reduction product was noted. After one day at room temperature, the anthrone content of the filtrate had increased to ~0.15%. Another sample, held for two additional days at 45 C, analyzed at 0.155% anthrone.

Example 2

Manufacture of the disodium salt of 9,10-dihydroxyanthracene on a larger scale was carried out in the following manner:

Equipment: A 1000 L jacketed reactor (glass-lined or stainless steel) with both cooling water and heated water to the jacket.

Bill of Materials:

| Compound | MW | Kg | Moles |
|---|---|---|---|
| Anthraquinone (AQ) | 208.22 | 120 | 576 |
| Formamidinesulfinic Acid (FAS) | 108.12 | 65 | 601 |
| Aq. Sodium Hydroxide (31%) | | 384 | |
| 100% basis | 40.01 | 119 | 2975 |
| Water | | 431 | |
| Total Weight | | 1000 | |

Procedure and Results:

Into a clean, dry reactor was charged 120 kg of anthraquinone, 65 kg of FAS and 431 kg of water. The order of addition is not critical. The vessel was purged with nitrogen and a nitrogen blanket was maintained in the reactor throughout the process. To the well-stirred slurry was next added the 31% anthraquinone sodium hydroxide over a period of ~20 minutes. Cooling was terminated and the reaction mass was heated to 40–45 C and held with continuous stirring for 120 minutes. The reaction mass was next cooled to 30 C and discharged under nitrogen through a bag filter to drums. The finished product was a clear ruby red liquid free from particulate matter. Specific gravity @20 C=1.204. Anthrahydroquinone, disodium salt assay (measured as AQ): 11.4% (95% of theory). The solution also contained 0.07% sodium anthranolate (measured as anthrone) Approximately 1 kg of solids, containing 57% AQ and 0.05% anthrone, was retained in the filter bag.

What is claimed is:

1. A process for the preparation of water-soluble salts of hydroquinones comprising reacting an aqueous liquid solution of (a) a formamidinesulfinic acid corresponding to the formula $R_2N-C(=NH)-SO_2H$, in which the R groups are independently selected from the group consisting of H and $C_{1-4}$ alkyl, and (b) alkali metal or quaternary ammonium hydroxide having dispersed therein (c) a quinone at a temperature of 10°–70° C. under an inert gaseous atmosphere, wherein the molar ratio of (b) to (a) is at least 4, and the molar ratio of (a) to (c) is at least 1.

2. The process of claim 1 in which the R groups of the acid are hydrogen.

3. The process of claim 1 in which the quinone is a polycyclic quinone.

4. The process of claim 3 which the polycyclic quinone is 9,10-anthraquinone.

5. The process of claim 1 in which the base is sodium hydroxide.

6. A water-soluble hydroquinone salt prepared by the process of claim 1.

7. The water-soluble hydroquinone salt of claim 6 which is the disodium salt of anthrahydroquinone.

* * * * *